United States Patent [19]
Oliverio

[11] Patent Number: 6,120,473
[45] Date of Patent: Sep. 19, 2000

[54] ARCH SUPPORTER

[76] Inventor: Catherine H. Oliverio, 235 Tyler Ave., Washinton, Pa. 15301

[21] Appl. No.: 09/252,114

[22] Filed: Feb. 18, 1999

[51] Int. Cl.⁷ .................................................. A61F 13/00

[52] U.S. Cl. ................................ 602/66; 602/41; 602/53; 602/54; 602/57

[58] Field of Search ........................... 602/53, 66, 41–59; 128/888, 889, 892, 893, 894; 36/31, 145, 166

[56] References Cited

U.S. PATENT DOCUMENTS

| | | | |
|---|---|---|---|
| 3,490,448 | 1/1970 | Grubb | 602/53 |
| 4,377,159 | 3/1983 | Hansen | 602/53 |
| 5,180,360 | 1/1993 | Rhame, Jr. | 602/74 |

*Primary Examiner*—Kim M. Lee

[57] ABSTRACT

An arch supporter for providing padded support to an arch region of a user's foot. The arch supporter includes a flexible panel with a resiliently deformable pad upwardly extended from a top face of the panel. The top face of the panel also has an adhesive thereon to permit adhesion to a user's foot.

7 Claims, 1 Drawing Sheet

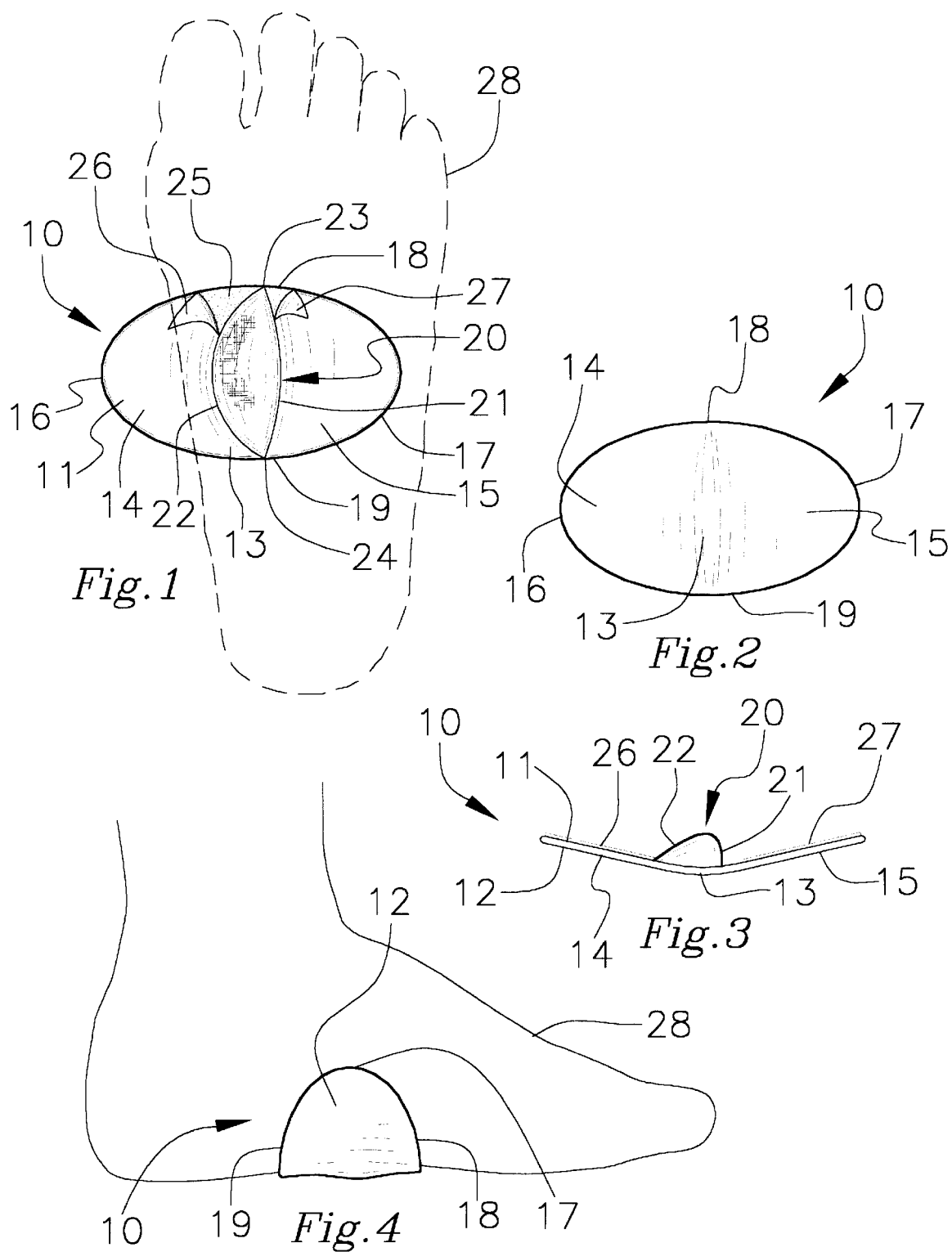

ARCH SUPPORTER

BACKGROUND OF THE INVENTION

1. Field of the Invention

The present invention relates to arch supporters and more particularly pertains to a new arch supporter for providing padded support to an arch region of a user's foot.

2. Description of the Prior Art

The use of arch supporters is known in the prior art. More specifically, arch supporters heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 2,330,398 by Vass; U.S. Pat. No. 4,170,233 by Bunsick; U.S. Pat. No. Des. 336,718 by Scroer, Jr.; U.S. Pat. No. 2,286,495 by Matteson; U.S. Pat. No. 5,463,824 by Barna; and U.S. Pat. No. Des. 353,259 by Schroer, Jr.

While these devices fulfill their respective, particular objectives and requirements, the aforementioned patents do not disclose a new arch supporter. The inventive device includes a flexible panel with a resiliently deformable pad upwardly extended from a top face of the panel. The top face of the panel also has an adhesive thereon to permit adhesion to a user's foot.

In these respects, the arch supporter according to the present invention substantially departs from the conventional concepts and designs of the prior art, and in so doing provides an apparatus primarily developed for the purpose of providing padded support to an arch region of a user's foot.

SUMMARY OF THE INVENTION

In view of the foregoing disadvantages inherent in the known types of arch supporters now present in the prior art, the present invention provides a new arch supporter construction wherein the same can be utilized for providing padded support to an arch region of a user's foot.

The general purpose of the present invention, which will be described subsequently in greater detail, is to provide a new arch supporter apparatus and method which has many of the advantages of the arch supporters mentioned heretofore and many novel features that result in a new arch supporter which is not anticipated, rendered obvious, suggested, or even implied by any of the prior art arch supporters, either alone or in any combination thereof.

To attain this, the present invention generally comprises a flexible panel with a resiliently deformable pad upwardly extended from a top face of the panel. The top face of the panel also has an adhesive thereon to permit adhesion to a user's foot.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new arch supporter apparatus and method which has many of the advantages of the arch supporters mentioned heretofore and many novel features that result in a new arch supporter which is not anticipated, rendered obvious, suggested, or even implied by any of the prior art arch supporters, either alone or in any combination thereof.

It is another object of the present invention to provide a new arch supporter which may be easily and efficiently manufactured and marketed.

It is a further object of the present invention to provide a new arch supporter which is of a durable and reliable construction.

An even further object of the present invention is to provide a new arch supporter which is susceptible of a low cost of manufacture with regard to both materials and labor, and which accordingly is then susceptible of low prices of sale to the consuming public, thereby making such arch supporter economically available to the buying public.

Still yet another object of the present invention is to provide a new arch supporter which provides in the apparatuses and methods of the prior art some of the advantages thereof, while simultaneously overcoming some of the disadvantages normally associated therewith.

Still another object of the present invention is to provide a new arch supporter for providing padded support to an arch region of a user's foot.

Yet another object of the present invention is to provide a new arch supporter which includes a flexible panel with a resiliently deformable pad upwardly extended from a top face of the panel. The top face of the panel also has an adhesive thereon to permit adhesion to a user's foot.

Still yet another object of the present invention is to provide a new arch supporter that helps reduce foot pain.

Even still another object of the present invention is to provide a new arch supporter that has an adhesive to attach the supporter to the user's foot so that the user may have arch support when walking in bare feet or in sandals.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic top view of a new arch supporter according to the present invention with the position of a user's foot illustrated in phantom lines.

FIG. 2 is a schematic bottom view of the present invention.

FIG. 3 is a schematic side view of the present invention.

FIG. 4 is a schematic side view of the present invention in use on the foot of a user.

DESCRIPTION OF THE PREFERRED EMBODIMENT

With reference now to the drawings, and in particular to FIGS. 1 through 4 thereof, a new arch supporter embodying the principles and concepts of the present invention will be described.

As best illustrated in FIGS. 1 through 4, the arch supporter generally comprises a flexible panel with a resiliently deformable pad upwardly extended from a top face of the panel. The top face of the panel also has an adhesive thereon to permit adhesion to a user's foot.

In closer detail, the arch supporter comprises a flexible panel 10 with top and bottom faces 11,12, and a generally oval outer perimeter. The panel is divided into a central portion 13 interposed between a pair of end portions 14,15. The outer perimeter of the panel has a pair of arcuate end regions 16,17, and a pair of arcuate side regions 18,19 extending between the end regions of the outer perimeter of the panel. Each end portion of the panel is positioned adjacent a corresponding end region of the outer perimeter of the panel.

A resiliently deformable pad 20 is extended from the top face of the panel. The pad ideally comprises a resiliently deformable foamed material for optimal comfort and lightness of weight. Preferably, the pad is upwardly extended from the top face of the panel at least ¼ inch and ideally between about ½ inch and about 2 inches. The pad is positioned on the center portion of the panel and has an arcuate or domed upper face with a concavity facing downwards towards the top face of the panel.

The pad has an outer perimeter which comprises a pair of arcuate sides 21,22. The arcuate sides of the outer perimeter of the pad converge together at a pair of opposite pointed ends 23,24 of the outer perimeter of the pad. As best illustrated in FIG. 1, a first of the arcuate sides 21 of the outer perimeter of the pad preferably has a radius of curvature greater than a second of the arcuate sides 22 of the outer perimeter of the pad so that the second arcuate side has a sharper curve than the first arcuate side. Preferably, the first arcuate side of the pad has a slope defined from the top face of the panel between about 45 degrees and about 90 degrees. Ideally, the slope of the first arcuate side is between about 80 degrees and about 90 degrees. Preferably, the second arcuate side of the pad has a slope defined from the top face of the panel less than about 60 degrees. Ideally, the slope of the first arcuate side is about 45 degrees. With reference to FIG. 1, the pad is extended substantially across the center portion of the panel such that one of the pointed ends of the outer perimeter of the pad is positioned adjacent one of the side regions of the outer perimeter of the panel and the other of the pointed ends of the outer perimeter of the pad is positioned adjacent the other of the side regions of the outer perimeter of the panel.

The top face of the panel has an adhesive 25 thereon for adhesively coupling the top face of the panel to a foot of a user. Preferably, the adhesive is substantially coextensive on the top face of the panel with the end portions of the panel. A pair of peelable backings 26,27 substantially cover the adhesive on the top face of the panel. One of the backings is positioned on one of the end portions of the panel and the other of the backings is positioned on the other of the end portions of the panel. In use, the backings are designed for removal from the top face of the panel without substantially removal of the adhesive from the top panel to permit adhesive coupling of the top face of the panel to the foot of a user with the adhesive after the backings are removed.

In use, the arch supported is designed for providing comfort to a user's foot 28 having a sole, an arch region, and a pair of sides. As best illustrated in FIGS. 1 and 4, the top face of the panel is positioned adjacent the sole of the user's foot such that the pad is positioned beneath the arch region and the end portions of the panel extend towards opposite sides of the user's foot. Preferably, the first arcuate side of the pad is positioned on the foot in an inner direction towards the user's other foot and the second arcuate side of the pad is positioned facing towards the outside of the user's foot. The end portions of the panel are adhesively coupled to the sides of the user's foot with the adhesive on the top face of the panel.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An arch supporter, comprising:

a flexible panel having top and bottom faces;

a resiliently deformable pad being extended from said top face of said panel;

said top face of said panel having an adhesive thereon;

wherein said panel has a generally oval outer perimeter comprising a pair of arcuate end regions, and a pair of arcuate side regions extending between said end regions of said outer perimeter of said panel;

wherein said pad has an outer perimeter comprising a pair of arcuate sides, said arcuate sides of said outer perimeter of said pad converging together at a pair of opposite pointed ends of said outer perimeter of said pad, said pad being extended substantially across a center portion of said panel such that one of said pointed ends of said outer perimeter of said pad is positioned adjacent one of said side regions of said outer perimeter of said panel, and the other of said pointed ends of said outer perimeter of said pad is positioned adjacent the other of said side regions of said outer perimeter of said panel; and wherein said pointed ends of said pad are adapted for aligning along the side of the foot of the user to maintain alignment of said pad with the arch of the foot such that said pad is prevented from creating discomfort to the foot of the user by becoming positioned under the foot during use.

2. The arch supporter of claim 1, wherein a first of said arcuate sides of said outer perimeter of said pad has a radius of curvature greater than a second of said arcuate sides of said outer perimeter of said pad.

3. The arch supporter of claim 2, wherein said first arcuate side of said pad has a slope defined from said top face of said panel between about 45 degrees and about 90 degrees, and wherein said second arcuate side of said pad has a slope defined from said top face of said panel less than about 60 degrees.

4. The arch supporter of claim 3, wherein said slope of said first arcuate side is between about 80 degrees and about 90 degrees, and wherein said slope of said first arcuate side is about 45 degrees.

5. The arch supporter of claim 1, wherein said panel has a central portion on said panel interposed between a pair of end portions of said panel, and wherein said pad is positioned on said center portion of said panel.

6. The arch supporter of claim 1, wherein said pad comprises a resiliently deformable foamed material.

7. An arch supporter, comprising:

a flexible panel having top and bottom faces, a generally oval outer perimeter, and a central portion on said panel interposed between a pair of end portions of said panel;

said outer perimeter of said panel having a pair of arcuate end regions, and a pair of arcuate side regions extending between said end regions of said outer perimeter of said panel;

each of said end portions of said panel being positioned adjacent a corresponding end region of said outer perimeter of said panel;

a resiliently deformable pad being extended from said top face of said panel, said pad comprising a resiliently deformable foamed material;

wherein said pad is upwardly extending from said top face of said panel at least ¼ inch;

said pad being positioned on said center portion of said panel;

said pad having an arcuate upper face having a concavity facing towards said top face of said panel;

said pad having an outer perimeter comprising a pair of arcuate sides, said arcuate sides of said outer perimeter of said pad converging together at a pair of opposite pointed ends of said outer perimeter of said pad;

a first of said arcuate sides of said outer perimeter of said pad having a radius of curvature greater than a second of said arcuate sides of said outer perimeter of said pad such that said second arcuate side has a sharper curve than the first arcuate side;

said pad being extended substantially across said center portion of said panel such that one of said pointed ends of said outer perimeter of said pad is positioned adjacent one of said side regions of said outer perimeter of said panel, and the other of said pointed ends of said outer perimeter of said pad is positioned adjacent the other of said side regions of said outer perimeter of said panel;

said first arcuate side of said pad having a slope defined from said top face of said panel between about 80 degrees and about 90 degrees;

said second arcuate side of said pad having a slope defined from said top face of said panel of about 45 degrees;

said top face of said panel having an adhesive thereon, said adhesive being adapted for adhesively coupling said top face of said panel to a foot of a user, said adhesive being substantially coextensive on said top face of said panel with said end portions of said panel;

a pair of peelable backings substantially covering said adhesive on said top face of said panel, one of said backings being positioned on one of said end portions of said panel and the other of said backings being positioned on the other of said end portions of said panel;

said backings being adapted for removal from said top face of said panel without substantially removing said adhesive from said top panel to permit adhesive coupling of said top face of said panel to the foot of a user with said adhesive after said backings are removed;

said top face of said panel being positioned adjacent the sole of the foot such that said pad is positioned beneath the arch and said end portions of said panel extend towards the sides of the foot, said end portions of said panel being adhesively coupled the foot of the user with said adhesive of said on said top face of said panel; and wherein said pointed ends of said pad are adapted for aligning along the side of the foot of the user to maintain alignment of said pad with the arch of the foot such that said pad is prevented from creating discomfort to the foot of the user by becoming positioned under the foot during use.

* * * * *